United States Patent [19]

Conradi

[11] 4,212,207
[45] Jul. 15, 1980

[54] ULTRASONIC TUBE INSPECTION

[75] Inventor: Joseph J. Conradi, Houston, Tex.

[73] Assignee: Shell Oil Company, Houston, Tex.

[21] Appl. No.: 969,743

[22] Filed: Dec. 14, 1978

[51] Int. Cl.³ ........................................... G01N 29/04
[52] U.S. Cl. .................................................... 73/623
[58] Field of Search .................. 73/623, 622, 637, 627

[56] References Cited
U.S. PATENT DOCUMENTS

| 3,636,778 | 1/1972 | Huffstetler | 73/622 |
| 4,008,603 | 2/1977 | Paulissen | 73/623 |

Primary Examiner—Anthony V. Ciarlante

[57] ABSTRACT

A method and apparatus for graphically displaying the measurements obtained with an ultrasonic inspection instrument of the pulse-echo type. The instrument is designed to inspect tubular members for primarily internal corrosion and display the results on the face of a cathode ray tube.

17 Claims, 3 Drawing Figures

U.S. Patent Jul. 15, 1980 Sheet 1 of 3 4,212,207
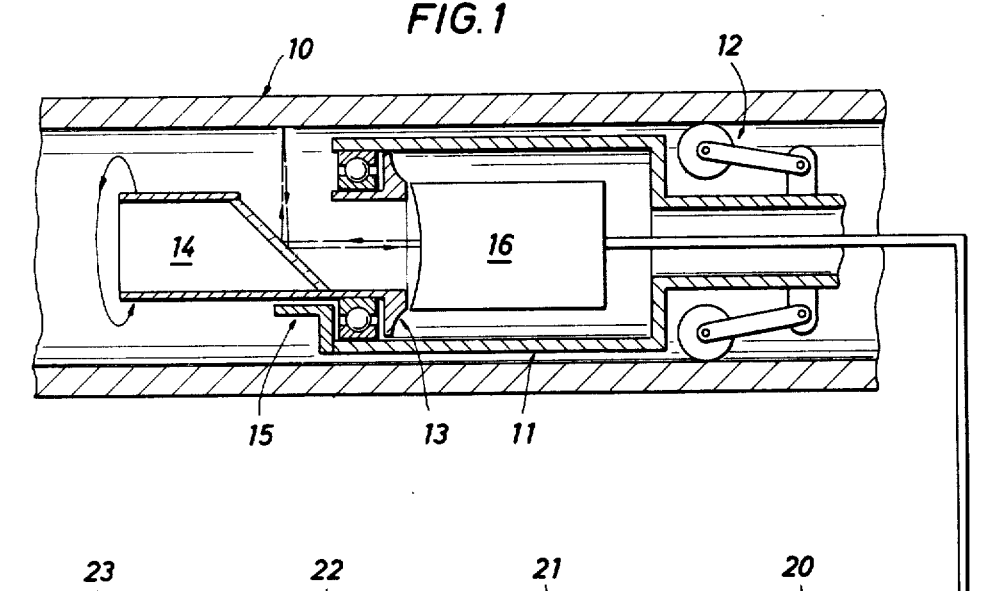
FIG. 1
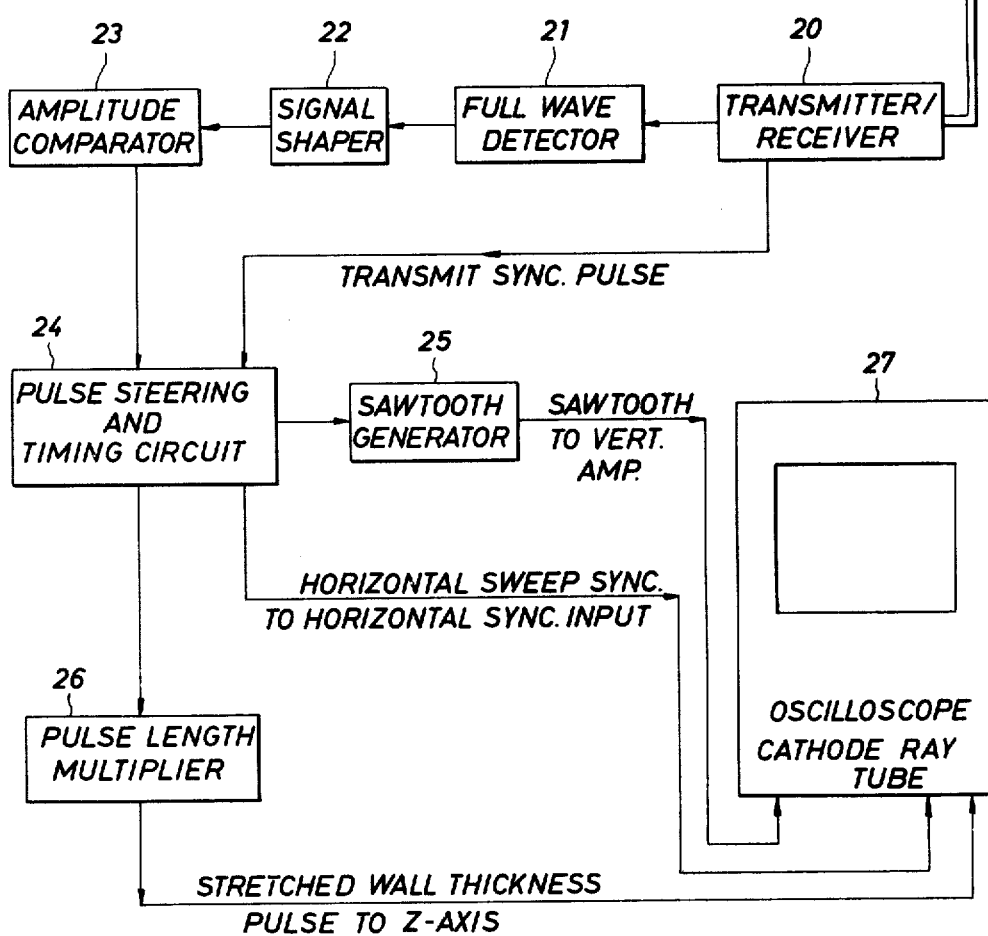

KINESCOPE PICTURE

|← 0.7" ID ——→|←—— 1.0" OD POSITION

A. CALIBRATION - TOOL PATTERN
1 MAJOR GRATICULE DIVISION ≈ 0.05"

B. USED HEAT EXCHANGER TUBE
MINIMUM WALL BY ULTRASONICS 0.040"
MINIMUM WALL BY MICROMETER 0.038"

ULTRASONIC TUBE INSPECTION

RELATED PATENT

The present invention is an improvement in the ultrasonic inspection tool disclosed in U.S. Pat. No. 4,008,603 issued on Feb. 22, 1977.

BACKGROUND OF THE INVENTION

The present invention relates to an ultrasonic method for inspecting tubular members for internal corrosion and particularly to a method for displaying the results of the inspection. The above referenced patent discloses an ultrasonic inspection tool of the pulse-echo type having a probe adapted to be moved through the tubular member. The probe includes an ultrasonic transducer which produces ultrasonic waves that are directed normally to the wall of the tubular member by a rotating 45-degree mirror. The transducer is energized to transmit an acoustic pulse and then acts as a receiver to receive the echoes or reflections of the acoustic pulse from the inner and outer walls of the tubular member. The referenced patent also discloses the measuring of the time interval between the reflection of the acoustic energy from the inner and outer walls of the tubular member. The time intervals are then segregated according to their magnitude by a distribution analyser and recorded on separate recorders, the number of counts in each recorder being proportional to the area having a thickness in the range shown for the recorder. The presence of a large number of short time intervals would indicate extensive thinning of the tube wall by corrosion. If all of the time intervals fell within a relatively narrow range, it would indicate uniform wall thickness and the absence of any corrosion.

The above recording system has several problems which reduced the effectiveness of the inspection tool. For example, the rough inner wall of a corroded tube scatters and attenuates the ultrasonic pulse so that the pulse reflected from the outer wall may be too small to be detected. In this event, the wall thickness measurement is missed. A rough inner wall can also cause multiple reflections from the inner wall. Since the interval between these reflected pulses is not related to the wall thickness, they produce false measurements of the wall thickness. Finally, overlap of the outer wall reflection by the much larger inner wall reflection prevents measuring walls thinner than about 0.05 inches. Because the more severely corroded and rougher areas produce a larger percentage of missed measurements, the measurements that are made are biased in favor of the smoother and less corroded areas. Furthermore, the false measurements obscure the valid measurements, especially in the low range of measurable thickness. These problems, combined with the limit on the minimum measurable thickness, make it impossible to make a reliable assessment of the extent and severity of the corrosion damage.

These problems are largely avoided in the present invention.

BRIEF DESCRIPTION OF THE INVENTION

The present invention utilizes the probe and the transmitter/receiver of the above invention but provides an improved display system. In particular, the invention uses a cathode ray oscilloscope to display the actual measurement signals. By a process similar to that used in television, the ultrasonic pulses reflected from the inner and outer walls are used to produce a rectilinear picture of the circumferential cross section of the tube wall.

The picture is produced as follows: A horizontal sweep of the oscilloscope electron beam is made to occur each time the transducer emits an ultrasonic pulse. The sweep is delayed, however, by a fixed, preset time to allow expanding the interval of interest around the wall reflections. The inner and outer wall reflections are used to initiate and terminate a rectangular voltage pulse. The duration of this pulse is then increased 3.87 times to compensate for the different sonic velocities in water and steel, and this stretched voltage pulse is used to brighten the electron trace for its duration. The length of the bright portion of the horizontal trace is, therefore, proportional to the wall thickness, and the positions of the beginning and end of the bright trace are proportional to the distances between the rotational axis of the mirror and the inner and outer walls. The probe is provided with a target which reflects a portion of the ultrasonic pulse each time the rotating mirror passes the location of the target. This reflected energy is used as a signal to synchronize a saw-tooth voltage with the rotation of the mirror. The sawtooth voltage is applied to the vertical deflection plates of the oscilloscope and causes successive horizontal sweeps to be displaced vertically by an amount proportional to the rotation of the mirror. Preferably, the vertical gain control of the oscilloscope is adjusted so that the complete vertical dimension of the cathode ray tube is utilized for each scan of the tubular wall. Thus, the oscilloscope screen displays all of the wall thickness measurements made during the complete scan of the circumference of the tube, which occurs with each revolution of the mirror.

The vertical array of horizontal bright lines produces, therefore, a stationary, bright picture of the circumferential cross section of the tube wall on a dark background. In this picture, the envelope of the left ends of the bright lines corresponds to the contour of the inner wall, and the right ends to the outer wall. The vertical height of the picture corresponds to the circumference, and the width to the wall thickness.

As the probe is moved through the tube, the picture changes, of course, as the contours change.

Missed measurements result in bright lines that extend all the way to the right edge of the screen. False measurements result in bright lines that may terminate anywhere, but in general, terminate at positions clearly inconsistent with the known position of the outer wall. Missed and false measurements are, therefore, easily recognized and can be compensated for by extrapolating, in the mind's eye of the operator, the contour of the outer wall where it is shown through the places where it is not shown. This extrapolation permits measuring the wall thickness everywhere in spite of missed and false measurements and pits where the wall is too thin to be measured directly.

The ability to reconstruct the missing portions of the outer wall contour requires that the outer wall of the tube not be significantly disfigured by corrosion. External corrosion can be recognized, however, if the number of missed and false measurements is small.

BRIEF DESCRIPTION OF THE DRAWINGS

The invention will be more easily understood from the following detailed description of a preferred embodiment when taken in conjunction with the attached drawings showing:

FIG. 1—A block diagram of a system for carrying out the invention;

DESCRIPTION OF THE PREFERRED EMBODIMENT

Figure 2:
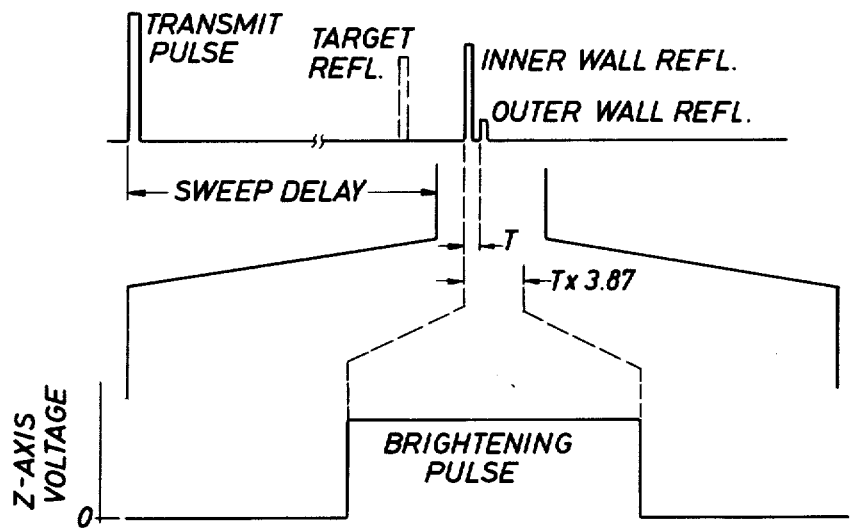
FIG. 2—A stylized drawing of the oscilloscope display.
Figure 2:
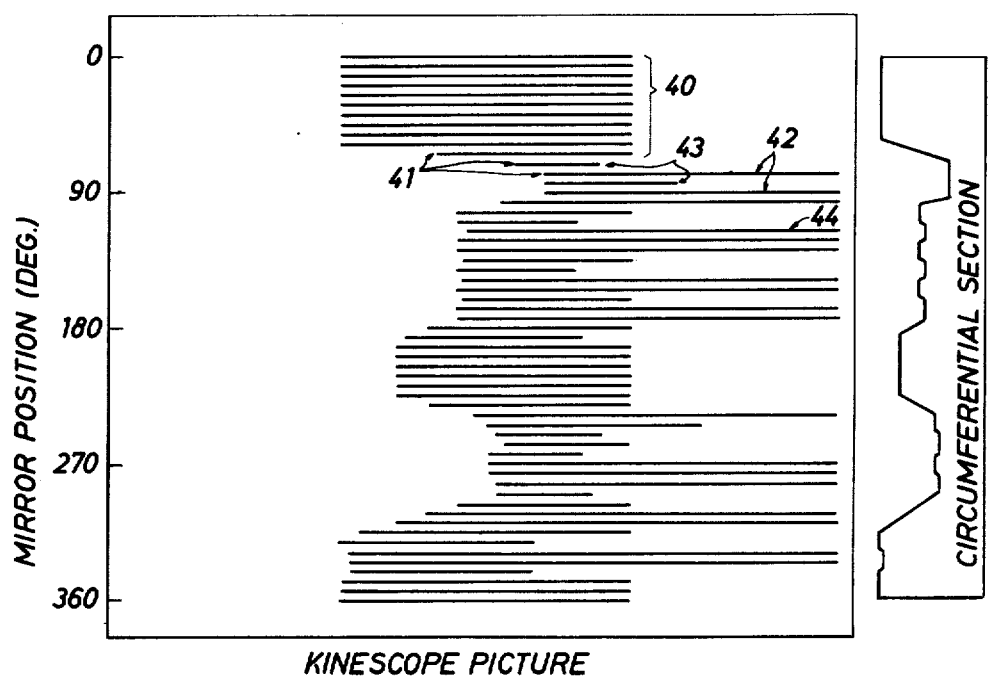

FIG. 1 shows the tubular member 10 and the probe 11 as shown in the prior patent, including the transducer 16 and the rotating mirror 14. The probe is provided with a centering means 12 and a turbine 13 for driving the mirror 14. A small target 15 is attached to the probe housing and disposed in the path of the ultrasonic energy to produce a target pulse which provides a synchronizing signal. The transducer is mounted in the body of the probe and serves as both a transmitter and receiver. The transducer is connected to the transmitter/receiver 20, full-wave detector 21, signal shaping circuit 22, and an amplitude comparator 23 shown in the prior patent. As explained in the prior patent, the transmitter/receiver and transducer are commercially available from Panametrics Incorporated, Waltham, Mass. The full wave detector rectifies the ultrasonic signals and the signal shaping circuit optimizes the signal shape to improve the resolution between the inner and outer wall pulses. The constant amplitude output pulses from the comparator are then fed to the pulse steering and timing circuit 24, which separates the target pulse from the wall pulses, and produces synchronizing pulses for the sawtooth generator 25 and for the horizontal sweep generator in the oscilloscope 27. Timing in this circuit is initiated by the transmit sync. pulse from the transmitter/receiver. The pulse steering and timing circuit also produces a wall thickness pulse whose duration is equal to the time between the inner and outer wall pulses. This wall thickness pulse is fed to the pulse length multiplier 26, which increases the pulse duration 3.87 times. This stretched pulse is then fed to the Z-axis of the oscilloscope to brighten the trace. The output of the sawtooth generator is fed to the vertical deflection amplifier of the oscilloscope.

The small target 15 is mounted on the probe and positioned so that it will intercept the ultrasonic energy that is reflected from the face of the rotating mirror radially outward toward the wall of the tube. In particular, the target 15 may be a small metal target that will reflect only a small part of the ultrasonic energy so that it does not obscure any part of the tube. The pulse reflected from the target provides a synchronizing signal once for each rotation of the rotating mirror. This synchronizing signal is separated from the wall signals in a pulse steering and timing circuit 24 and is used to trigger a sawtooth generator 25. The sawtooth generator then produces a linearly rising voltage until the next target signal. The next target signal resets the sawtooth voltage to the starting point and the cycle is repeated. One cycle of the sawtooth voltage is produced, therefore, for each revolution of the mirror.

Referring to FIG. 2, there is shown the pulses produced by the probe curcuits and a stylized display on the cathode ray tube 27. At the top of the drawing there is shown the time sequence of signals produced when the transducer is energized and when the reflections from the target and inner and outer walls are received. The target pulse is shown in dashed lines to indicate that it occurs only once for each revolution of the mirror, whereas about two hundred ultrasonic pulses, and corresponding horizontal sweeps, are produced during each revolution. The voltage pulse used to brighten the trace is shown below the wall signals. The dashed trihedral lines are intended to show that the pulse is started by the inner wall signal but that its duration is 3.87 times the time between the wall signals, which is the ratio of the velocity of sound in the steel tube to that in water. It should be noted that the initiation of the horizontal sweep is delayed and that the sweep covers the small interval around the wall signals. This is indicated by the solid trihedral lines. Delaying the sweep makes it possible to expand the region around the wall signals.

Below the brightening pulse is shown a stylized drawing of the oscilloscope picture that would be produced by the arbitrary circumferential cross section of the tube shown at the right. The upper end of the tube section has a uniform thickness and produces the corresponding bright lines 40 of equal length. The walls are taken to be smooth in this region so none of the measurements are missed. As the mirror turns and scans the ultrasonic beam across the deep pit, the left ends of the bright lines 41 retreat to the right and reproduce the inner wall contour. The wall thickness in this deep pit is taken to be smaller than can be measured. In this case, the inner wall reflection overlaps the outer wall reflection. Since the outer wall reflection is not detected, the bright lines extend all the way to the right 42. Also shown here, and elsewhere in this picture, are some lines 43 whose terminations do not conform with the known position of the outer wall. These are false measurements of the wall thickness and are produced by multiple reflection of the ultrasonic pulse at the rough inner wall. Multiple reflection can result in two pulses reflected back to the transducer that are separated in time and are indistinguishable from the usual pair of pulses reflected from the inner and outer walls. Below the deep pit is a region of uniform thickness but with a rough inner wall. The rough wall attenuates the reflected pulses by scattering. This sometimes reduces the already small outer wall reflection below the detection limit and causes some missed measurements 44. The rest of the picture simply repeats these features. The complete picture shows that the contour of the inner wall is explicitly shown everywhere because the strong inner wall reflections are seldom missed. The position of the outer wall is not explicitly shown everywhere because of missed and false measurements, but its position can be determined everywhere by extrapolating the position of the outer wall where it is shown through those regions where it is not shown. In this way the wall thickness can be estimated everywhere in spite of missed and false measurements and walls too thin to be measured directly, so long as the number of missed and false measurements is not too large.

Figure 3:
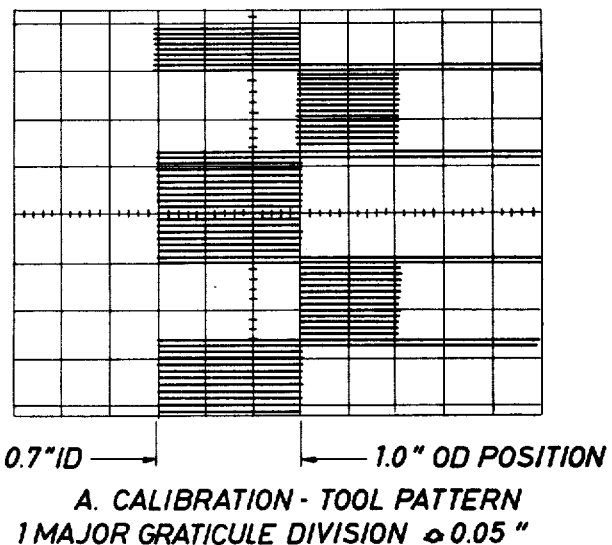
FIG. 3—An illustration of an actual oscilloscope display.
Figure 3:
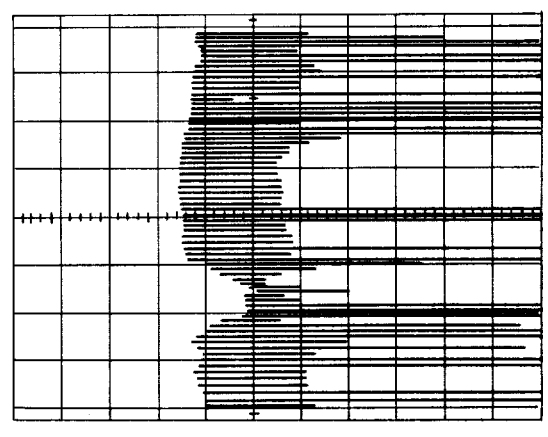

FIG. 3A is a depiction of a photograph of the scope display for a calibration tool. The calibration tool is used by the operator to set the position of the outer wall of a one-inch outside diameter tube at a convenient position on the scope. The calibration tool is a one-inch outside diameter steel tube with a 0.150-inch wall having two equally spaced 90 degree segments removed. An aluminum tube fits over the steel tube to provide a reflective surface where the segments are removed. This tool is also used to calibrate the instrument so that each major division of the graticule on the horizontal axis is equivalent to 0.050 inches of wall thickness.

FIG. 3B is a depiction of a photograph of the scope display of an actual used heat exchanger tube. The inspection tool of the present invention shows that the wall thickness in the deep pit is about 0.04 inches. In a separate measurement of this pit by hand with a micrometer, the wall thickness was found to be 0.038 inches. The slight S-shape on the inner and outer wall is the result of the probe being off center in the tube when the measurement was made.

While the inspection tool of this invention has been described in relation to the inspection of air-cooled heat exchanger tubes, it can be adapted for use with a wide variety of tubes. Of course, the delay between the production of the ultrasonic pulse and the initiating of the brighting of the sweep will vary. Likewise, the length of the pulse used for controlling the brightening of the sweep will vary with different tube sizes. Both of these variables can be adjusted to provide the most useful display.

I claim as my invention:

1. An improved ultrasonic apparatus of the pulse echo type for inspecting tubular members where the apparatus includes means for directing a pulse of ultrasonic energy through the wall of the tubular member, said improvement comprising:
    means for producing a plurality of pulses spaced circumferentially around the tubular member;
    first circuit means disposed to detect the reflection of said ultrasonic energy from the inner and outer walls of the tubular member,
    a cathode ray tube, the horizontal sweep of said tube being triggered by the production of said pulses of ultrasonic energy and the beam intensity being turned on by the detection of the reflection from the inner wall and turned off by the detection of the reflection from the outer wall; and
    means for triggering a separate horizontal sweep of the cathode ray tube for each pulse of ultrasonic energy, each separate sweep being vertically spaced from the preceding sweep such that a rectilinear picture of the circumferential cross section of the tube wall is produced.

2. The apparatus of claim 1 and in addition, means for spacing the number of horizontal sweeps of said cathode ray tube corresponding to one complete scan of the wall of the tubular member to utilize the complete vertical dimension of the cathode ray tube.

3. The apparatus of claim 1 or 2 and in addition, means for delaying the initiation of the horizontal sweep of the cathode ray tube for a pre-set time period after production of said ultrasonic energy.

4. The apparatus of claim 1 or 2 and in addition, means for expanding the time interval between the reflections from the inner and outer walls to provide a longer bright interval for each horizontal sweep.

5. The apparatus of claim 1 or 2 and in addition, a target disposed to reflect a part of said ultrasonic energy to provide a signal for synchronizing the vertical sweep of said cathode ray tube with said means for producing a plurality of pulses spaced circumferentially around the tubular member.

6. The apparatus of claim 1 or 2 and in addition, means for multiplying the time interval between the reflections from the inner and outer walls by the ratio of the velocity of sound in the material of the tubular member to that in a fluid used to transmit said pulse of ultrasonic energy.

7. The apparatus of claim 1 or 2 and in addition, means for multiplying the time interval between the reflections from the inner and outer walls by the ratio of the velocity of sound in a steel tubular member to that in water.

8. The apparatus of claim 1, wherein said first circuit means produce bright lines on said cathode ray tube inconsistent with said rectilinear picture upon failing to detect said reflection of said ultrasonic energy, said circuit means also producing bright lines inconsistent with said rectilinear picture upon detecting a false reflection.

9. An improved method for inspecting tubular members wherein a pulse of ultrasonic energy is directed through the wall of said tubular member, said improvement comprising:
    producing a plurality of pulses spaced circumferentially around said tubular member;
    detecting the reflection of said ultrasonic energy from the inner and outer walls of said tubular member;
    triggering the horizontal sweep of a cathode ray tube for each pulse of ultrasonic energy;
    vertically spacing each horizontal sweep from the preceding sweep; and,
    activating the beam intensity of said cathode ray tube by detecting the reflection from said inner wall and deactivating the beam intensity by detecting the reflection from said outer wall such that a rectilinear picture of the circumferential cross section of the tube wall is produced.

10. Method according to claim 9, including utilizing the complete vertical dimension of said cathode ray tube by spacing said horizontal sweep thereon.

11. Method according to claim 9, including delaying the initiation of said horizontal sweep for a preset time period after the production of said ultrasonic energy.

12. Method according to claim 11, including expanding the time interval between the reflections from the inner and outer walls to provide a longer bright interval for each horizontal sweep.

13. Method according to claim 9, including disposing a target to reflect a part of said ultrasonic energy for providing a signal to synchronize the vertical sweep of said cathode ray tube with the production of said plurality of pulses.

14. Method according to claim 9, including multiplying the time interval between the reflections from said inner and outer walls by the ratio of the velocity in the material in the tubular member to that in a fluid used to transmit said pulses of ultrasonic energy.

15. Method according to claim 9, including multiplying the time interval between the reflections from said inner and outer walls by the ratio of the velocity of sound in a steel tubular member to that in water.

16. Method according to claim 9, including producing bright lines on said cathode ray tube inconsistent with said rectilinear picture when a reflection of said ultrasonic energy is missed.

17. Method according to claim 9, including producing bright lines on said cathode ray tube inconsistent with said rectilinear picture when a false reflection is detected.

* * * * *